United States Patent [19]
Ferguson

[11] Patent Number: 5,195,378
[45] Date of Patent: Mar. 23, 1993

[54] DYNAMIC THERMAL-MECHANICAL MATERIAL TESTING SYSTEM UTILIZING A BALANCED MAGNETIC FIELD

[75] Inventor: Hugo S. Ferguson, Averill Park, N.Y.

[73] Assignee: Duffers Scientific, Inc., Poestenkill, N.Y.

[21] Appl. No.: 694,911

[22] Filed: May 2, 1991

Related U.S. Application Data

[63] Continuation-in-part of Ser. No. 672,690, Mar. 7, 1991, Pat. No. 5,092,179.

[51] Int. Cl.$^5$ .............................................. G01D 7/02
[52] U.S. Cl. ..................................................... 73/790
[58] Field of Search ................ 73/790, 794, 818, 825, 73/826, 837; 374/46-51

[56] References Cited

U.S. PATENT DOCUMENTS

| | | | |
|---|---|---|---|
| 2,375,032 | 5/1945 | Parke et al. | 73/95 |
| 2,685,195 | 8/1954 | Streblow | 73/15.6 |
| 3,100,253 | 8/1963 | O'Connor | 219/20 |
| 3,176,499 | 4/1965 | Sikora | 73/15.6 |
| 4,599,905 | 7/1986 | Vogel et al. | 73/830 |
| 4,687,343 | 8/1987 | Raffalski | 374/56 |
| 4,998,006 | 3/1991 | Perlman | 219/212 |
| 5,092,179 | 3/1992 | Ferguson | 73/790 |

OTHER PUBLICATIONS

R. L. Mehan et al, "The Use of Interrupted Resistance Heating to Perform Elevated Temperature Tensile Tests", Review of Scientific Instrumentation, vol. 45, No. 8, Aug. 1974, pp. 1022-1025.

W. F. Savage, "Some Observations on the Hot-Ductility of Austenitic Stainless Steels", Doctoral Thesis submitted to the Metallurgical Engineering Department of Rensselaer Polytechnic Institute; Troy, N.Y.; Jun. 1955, specifically photograph of FIG. 7 therein.

*Primary Examiner*—Robert Raevis
*Attorney, Agent, or Firm*—Peter L. Michaelson

[57] ABSTRACT

Apparatus for a dynamic thermal-mechanical material testing system that not only self-resistively heats and deforms a specimen, both under controlled conditions, but also substantially reduces adverse affects in specimen performance, such as magnetically induced motion and non-uniform specimen heating, that would otherwise result from magnetic fields which impinge upon the specimen and are caused by high heating currents flowing in the apparatus. This reduction is achieved by spatially locating high current carrying conductors used in the apparatus such that these conductors collectively generate substantially balanced, i.e. substantially equal, and opposite magnetic fields that effectively cancel each other out in a volumetric region in the apparatus which contains the specimen and particularly its work zone.

18 Claims, 2 Drawing Sheets

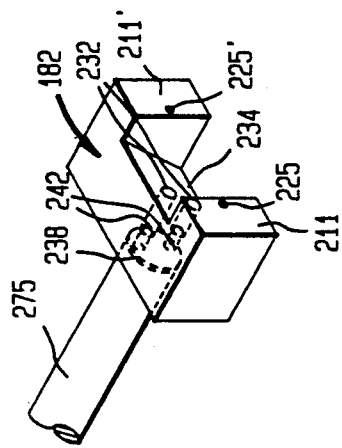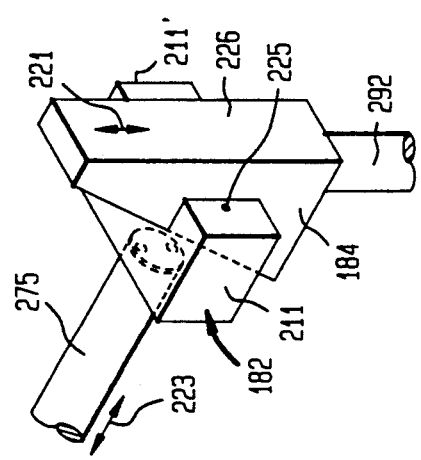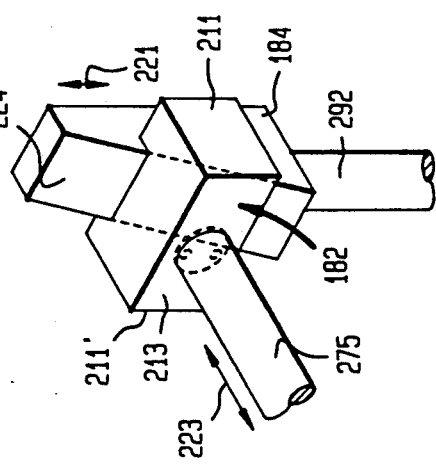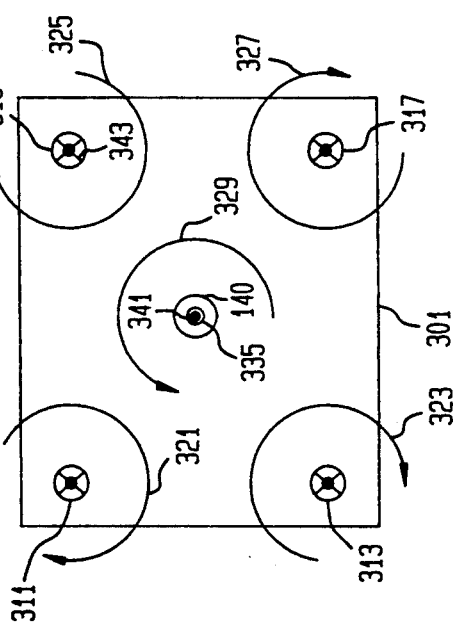

DYNAMIC THERMAL-MECHANICAL MATERIAL TESTING SYSTEM UTILIZING A BALANCED MAGNETIC FIELD

CROSS-REFERENCE TO RELATED APPLICATION

This application is a continuation-in-part of my co-pending patent application entitled "A DYNAMIC MATERIAL TESTING SYSTEM HAVING INDEPENDENT CONTROL OVER SPECIMEN DEFORMATION AND STRAIN RATE AND A METHOD FOR USE THEREIN" Ser. No. 07/672,690; filed Mar. 7, 1991, now U.S. Pat. No 5,092,179.

BACKGROUND OF THE DISCLOSURE

1. Field of the Invention

The invention relates to apparatus for a dynamic thermal-mechanical material testing system that not only self-resistively heats and deforms a specimen, under controlled conditions, but also substantially reduces adverse effects in specimen performance, such as magnetically induced motion or non-uniform specimen heating, that would otherwise result from magnetic fields which impinge upon the specimen and are caused by high heating currents flowing in the apparatus. This reduction is achieved by spatially locating high current carrying conductors used in the apparatus such that these conductors collectively generate substantially balanced, i.e. substantially equal, and opposite magnetic fields that effectively cancel each other out in a volumetric region of the apparatus which contains the specimen and particularly its work zone.

2. Description of the Prior Art

Metallic materials play an indispensable role as an essential component of an enormous number of different products. One crucial property of such materials is their ability to conduct electricity. Absent operation at superconductive temperatures, a metallic object possesses a resistance to electrical current flow based upon its cross-sectional size, length and resistivity. Owing to this resistance, the object will generate heat whenever an electric current is passed therethrough. This form of heating is the so-called "self-resistive heating". Self-resistive heating finds use in a wide number of diverse applications.

Different materials, including those that are metallic, possess widely varying mechanical, metallurgical and other properties. As such, the specific properties required of a material for use in a given application are first determined followed by selection of a specific material that exhibits appropriate minimum values of these properties. An essential step in selecting a specific material is first to determine its properties of interest by testing specimens of each such material being considered.

Materials are tested in a wide variety of different ways. One such way, which is experiencing substantially increasing use, is dynamic thermal-mechanical testing. Here, a specimen is held between two opposing anvils or gripped at each of its two ends in a jaw system. The specimen is typically in the form of a small cylinder or sheet section of a given material and has a substantially uniform circular, rectangular or square cross-sectional area. An electric current is serially passed from one anvil (or jaw assembly) through the specimen and to the other anvil (or jaw assembly) to generate, through self-resistive heating, a rapid, but controlled, heating rate throughout the specimen. Self-resistive heating is used inasmuch as it can produce very high material temperatures, such as in excess of 3000 degrees C., that are only limited by the melting range of the material. While the specimen is being self-resistively heated, various measurements are made of the specimen. Depending upon the specific measurements being made, the specimen either may or may not undergo controlled deformation while it is being heated. If the specimen is to be deformed, then this deformation can be accomplished by moving one of the two anvils (or jaw assemblies), at a controlled rate with respect to the other, in order to impart, e.g., a controlled compressive or tensile force to the specimen. Physical measurements, such as illustratively specimen dilation and temperature, are typically made while heating and deformation are simultaneously occurring. This testing not only reveals various properties of the specimen material itself, such as its continuous heating transformation curve, but also various dynamic properties, such as illustratively hot stress vs. strain rates and hot ductility; the dynamic properties being particularly useful in quantifying the behaviour of the material that will likely occur during rolling, forging, extrusion or other material forming and/or joining operations. One system that provides excellent dynamic thermal-mechanical testing is the GLEEBLE 2000 system manufactured by Duffers Scientific, Inc. of Poestenkill, New York (which also owns the registered trademark "GLEEBLE" and is the present assignee). This system advantageously heats the specimen in a manner, using direct self-resistive heating, that is expected to generate transverse isothermal planes throughout the entire specimen. Specifically, since each specimen generally has a substantially uniform transverse cross-section throughout its length, then, for low frequency current, the current density is expected to be uniform throughout the entire specimen which will cause uniform heating over the entire cross-section.

In order to produce the requisite level of self-resistive heating throughout the specimen, relatively high currents, typically on the order of several thousand amperes or more, must be passed through the specimen to produce a desired heating rate and specimen temperature. The amount of this current generally depends upon a number of factors, for example: the specific heat of the material; its resistivity; the geometric shape of the specimen, such as its cross-sectional area and length; heat loss from the specimen to its surroundings, principally including but not limited to the anvils (or jaw assemblies); and the value of the final temperature to be attained. In practice and owing to the low resistances of most specimens, generally only a few volts or less need to be applied across the specimen to conduct the required heating current therethrough.

Within such a testing system, the heating current must be routed through suitable conductors between a power supply, frequently a transformer secondary, and both anvils (or jaw assemblies). These conductors frequently take the form of either flexible wire of an appropriate gauge or, as in the GLEEBLE 2000 system, so-called "rolling flexible conductors" that contain a number of copper strips that have been laminated together. In either case, these large currents generate appreciable magnetic fields around the conductors.

The applicant has discovered that since a portion of these conductors is often situated in the vicinity of the specimen, then, during heating, a significant non-uniform magnetic field is produced by these conductors which extends throughout a volumetric region occupied by the specimen. This field tends to adversely affect specimen testing, and specifically specimen performance, in two ways. First, this field induces non-uniform current flow in the specimen that, when combined with the uniform current density established by the heating current flowing through the specimen, causes the total current density to vary throughout the specimen. This, in turn, causes undesired local variations in the temperature of the specimen. For specimens with relatively small cross-sectional area, these variations remain small and are generally insignificant. However, as specimens of increasing cross-sectional area are used, such as a 10 mm bar, these variations correspondingly increase and can be quite noticeable. These variations also increase and can become quite pronounced as the specimen undergoes heating and grows in width as the result of a simultaneously occurring compressive deformation. As such, it is well known in the art of material testing that as large specimens are used, these specimens must be properly positioned within a dynamic thermal-mechanical material testing system such that a relatively constant distance, particularly during the course of compressive deformation, can be maintained between the specimen and all high current conductors. Unfortunately, since such a position greatly depends upon the particular specimen being used, e.g. its geometry and magnetic properties, and the specific amount of deformation it will encounter, determining such a position has proven to be quite tedious and often difficult in practice. Second, the non-uniform field, typically occurring at a 50 or 60 Hz power line frequency, induces mechanical motion in the specimen, specifically causing it to noticeably vibrate. This motion, if it occurs with a sufficiently large amplitude, can generate substantial stress in the specimen, which, in turn, can induce unwanted strain therein, i.e. a change in material shape. The strain, if sufficiently large, can corrupt certain test results. In addition, this stress can be particularly troublesome if the specimen is to be heated in a stress-free manner. In this regard, ferrous specimens, with a relatively large surface area and if heated with sufficiently large currents, can disadvantageously exhibit significant amounts of induced motion. Since, in general, such materials, typified by many steel alloys, are extremely important from a commercial standpoint, it is imperative to obtain test results from a thermal-mechanical material testing system that are as accurate as possible for these materials.

Thus, a need exists in the art for a dynamic thermal-mechanical material testing system, and specifically for apparatus for inclusion therein, that substantially eliminates the adverse affects on specimen performance which would otherwise result from appreciable non-uniform magnetic fields that impinge upon the specimen and are generated by the high heating currents flowing through the apparatus.

SUMMARY OF THE INVENTION

My invention advantageously overcomes the adverse effects associated with dynamic thermal-mechanical material testing systems known in the art that self-resistively heat a specimen—particularly, though not exclusively including those with a relatively large cross-sectional area—and, in so doing, generate a non-uniform magnetic field therein.

Advantageously, my inventive apparatus splits the conduction path of the electrical current into a plurality of parallel paths that are spatially located so as to collectively generate a plurality of magnetic fields that effectively balance and cancel each other out in a volumetric region that contains the specimen. As such, the high heating current flowing through the apparatus itself to and from the specimen, does not generate any appreciable non-uniform magnetic fields in the specimen work zone. Consequently, my inventive apparatus substantially eliminates, even during compressive specimen deformation, any non-uniform heating in the work zone caused by induced current flow therein as well as magnetically induced specimen motion, either of which would be likely to otherwise result from a non-uniform magnetic field produced in the vicinity of the specimen and caused by high current flow through current carrying conductors used in thermal-mechanical material testing systems known in the art.

Specifically and in accordance with my inventive teachings, a test stand for use in a dynamic thermal-mechanical material testing system utilizes two opposing cross heads supported and spaced apart by two (or more) columns. Each column is conductive and provides a parallel path for heating current to flow between the cross heads. The specimen is situated along a longitudinal axis of the test stand with all components that transmit force to the specimen being located concentric therewith. During, illustratively, one half cycle of applied current flow, heating current flows through the specimen, splits illustratively in two equal portions with each portion flowing through one of the columns. Both portions then re-combine in the other cross head prior to flowing into a supply lead. The size and spatial location of each of the columns is chosen, for example as being symmetric with the longitudinal axis of the test stand, such that the magnetic fields generated by all of the columns effectively and substantially cancel in the volumetric region containing the specimen. In addition, the columns are preferably fabricated from a non-ferrous material in order to significantly reduce any magnetic interaction between these columns and rest of the test stand, including the specimen itself. Doing so, minimizes any eddy currents from being induced in the columns and any magnetizing thereof that might otherwise result from a magnetic field attributable to high current flow through any other high current conductor, including the specimen itself, used in the test stand.

BRIEF DESCRIPTION OF THE DRAWINGS

The teachings of the present invention can be readily understood by considering the following detailed description in conjunction with the accompanying drawings, in which:

FIGS. 2A and 2B respectively depict perspective and reverse perspective views of an assembly of wedge yoke 182 and wedge 184 both shown in FIG. 1;

FIG. 2C depicts a perspective view of wedge yoke 182 shown in FIG. 2A; and

FIG. 3 depicts a simplified end view, taken along lines 3—3 and in the direction indicated by the arrows associated therewith shown in FIG. 1, of a second embodiment of my inventive apparatus for inclusion in a test stand, such as stand 100, for use in a dynamic thermal-mechanical testing system.

To facilitate understanding, identical reference numerals have been used, where appropriate, to designate identical elements that are common to the figures.

DETAILED DESCRIPTION

Figure 1:
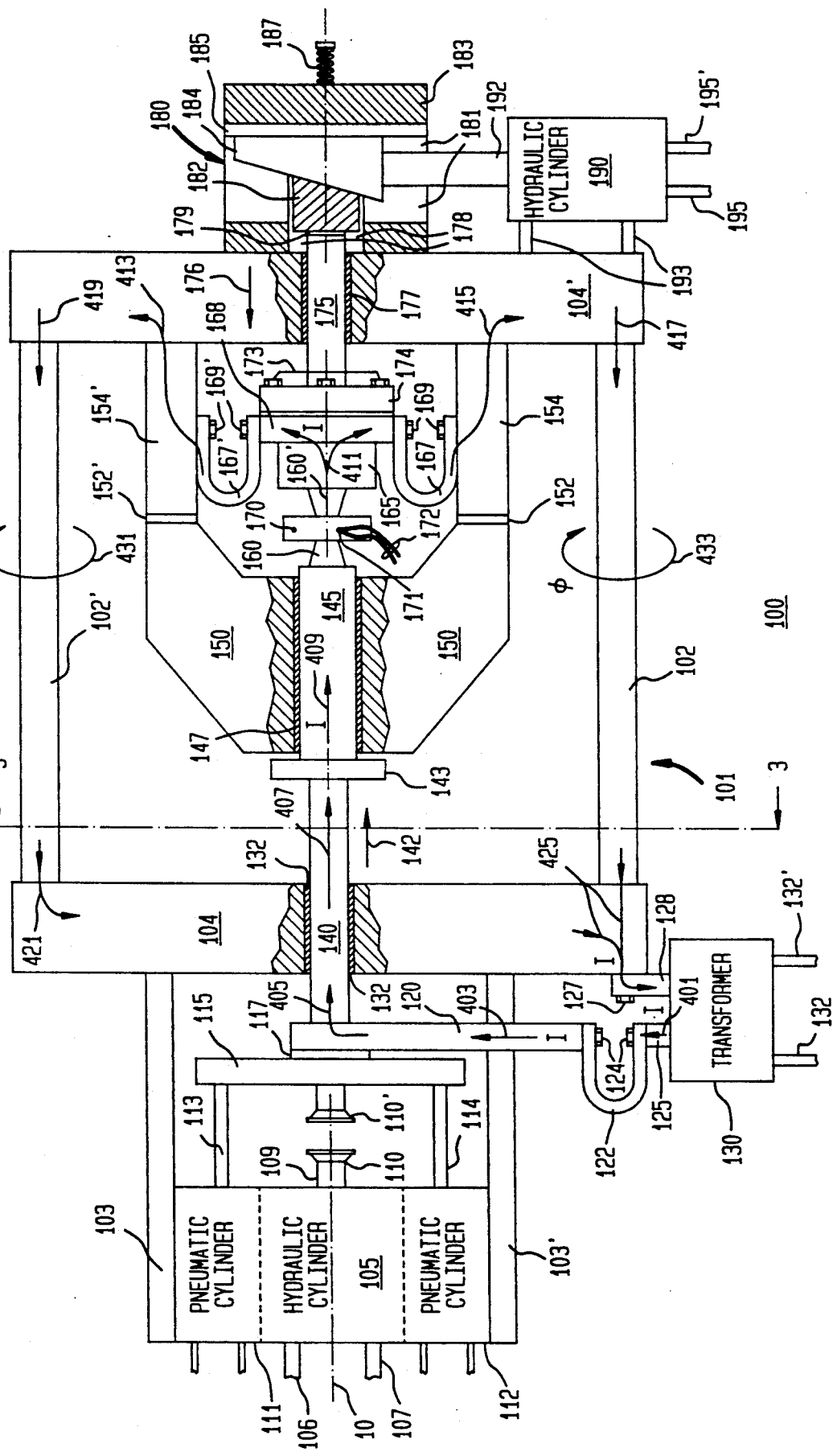
FIG. 1 is a schematic diagram, with partial cut-away views, of a test stand, for use in a dynamic thermal-mechanical testing system, that incorporates a first embodiment of my inventive apparatus.

After considering the following description, those skilled in the art will clearly realize that the broad teachings of my invention can be readily utilized in conjunction with any one of a variety of dynamic thermal-mechanical material testing systems for testing specimens of various materials. Nevertheless, for purposes of illustration and to simplify the following discussion, I will specifically describe my invention in the context of use with illustratively various portions of the GLEEBLE 2000 dynamic thermal-mechanical material testing system (which is hereinafter referred to merely as the GLEEBLE 2000 system; the GLEEBLE 2000 system is a successor to the GLEEBLE 1500 system and has similar control systems therein) manufactured by the Duffers Scientific, Inc. of Poestenkill, New York (which also owns the registered trademark "GLEEBLE" and is the present assignee hereof).

FIG. 1 depicts a schematic diagram, with partial cut-away views, of test stand 100 that incorporates a first embodiment of my inventive apparatus and is intended for use in conjunction with well-known control and monitoring circuitry and servo-controlled pneumatic and hydraulic systems found on the GLEEBLE 2000 dynamic thermal-mechanical testing system. Test stand 100 is capable of imparting independently programmed deformation and true strain rate to specimen 170 as well as a desired thermal profile thereto.

Generally speaking, in test stand 100, a specimen is oppositely situated between two anvils, each of which is movable with respect to the other. The portion of the specimen that is situated between both anvils and hence will undergo deformation is referred to hereinafter as the "work zone" of the specimen. Both anvils and the specimen are encircled by a stop assembly, illustratively containing a substantially U-shaped cross stop and twin stop bars extending therefrom to a first cross head which, in turn, is mounted to a frame. A first anvil is moved by a first shaft that extends through a second cross head which is also mounted to the frame. This shaft is pushed by a servo-hydraulically actuated piston (the "compression" piston), with the stroke of the shaft being limited by a stop plate, which is also part of the stop assembly, whenever that plate abuttingly engages against the cross stop. The second anvil, which abuts against an end of the specimen and is oppositely situated from the first anvil, is connected to one end of a second shaft which extends through the first cross head. The second shaft can be precisely positioned to incrementally move the specimen by a pre-defined distance towards the compression piston in order to control the exact amount of strain that will be imparted to the specimen by each successive hit. The velocity of the compression piston governs the velocity of the first anvil and hence the strain rate induced in the specimen during its compressive deformation.

Permitting the second anvil to be positionable independently of the stroke distance of the piston advantageously allows the deformation and true strain rate induced in the specimen to be independently controlled. The second anvil is moved, preferably through a wedge assembly actuated by another servo-hydraulically controlled piston, during the dwell time between successive deformations ("hits"). Appropriately positioning the second anvil and then relying on the stop plate rather than the compression piston to abruptly terminate both the travel of the piston during each hit and hence the strain induced in the specimen advantageously permits this piston to travel at substantially a controlled velocity throughout each entire compressive deformation. As such, a desired relatively high entrance true strain rate can be advantageously maintained in the specimen completely throughout each hit.

Additionally, my inventive test stand also has the capability to pass controlled amounts of alternating (AC) electric current through the specimen before, during and/or after each "hit" and also to conductively cool the specimen ends from an elevated temperature. This current causes the specimen to self-resistively heat and establish isothermal planes at a desired substantially uniform temperature throughout the work zone of the specimen. By controlling the rates at which the specimen work zone self-resistively heats and then conductively cools, the work zone can be dynamically set to experience any one of a wide range of different time dependent temperature profiles with relatively little, if any, thermal gradients appearing throughout the work zone. Furthermore, the conductors in test stand 100 that carry high heating currents are spatially located in the stand such that the magnetic fields generated thereby due to the flow of heating current therethrough effectively and substantially cancel each other out in a volumetric region of the stand that contains the specimen. Consequently, the specimen does not experience an appreciable magnetic field during heating and, as such, does not exhibit substantially any magnetically induced non-uniform heating or magnetically induced motion.

Although test stand 100 is shown in a horizontal orientation, the stand can be oriented to operate vertically, such as with a compressive stroke occurring in a downward direction, if desired. To simplify the discussion, all references to FIG. 1 will assume that the stand is oriented in a horizontal direction. Reference should also be made, where indicated during the course of the following discussion, to FIGS. 2A-2C which respectively depict perspective and reverse perspective views of an assembly of wedge yoke 182 and wedge 184 both shown in FIG. 1 and a perspective view of wedge yoke 182 shown in FIG. 2A.

As specifically shown in FIG. 1, test stand 100 contains frame 101 which is formed of two horizontal support columns (bars) 102 and 102' and two cross heads 104 and 104', with opposing ends of these bars fixedly secured in the cross heads. As described below, both these bars and the cross heads are fabricated from conductive materials. In addition, these components are rigidly constructed to withstand the physical forces occurring during compressive deformation of the specimen. Furthermore, each of these and other components, as discussed below, in test stand 100 has a high elastic modulus so as to exhibit relatively little elastic strain during specimen deformation. Stand 100 also contains hydraulic cylinder 105 and pneumatic cylinders 111 and 112 all mounted within a common block of material and secured, via braces 103 and 103', to frame 101 and specifically cross head 104. All these cylinders operate bi-directionally. Piston rods 113 and 114 of pneumatic cylinders 111 and 112 are rigidly attached to cross bar 115. This cross bar is rigidly connected, using non-conductive fasteners (not specifically shown), through insulating plate 117, to conductor 120 which, in turn, abuts against and is securely connected to one end of conductive shaft 140. Each of these fasteners is typically formed of a high strength bolt with an insulated sleeve situated around its shank, an insulated washer at its head and a back-up washer located between the insulated washer and the head. Shaft 140 rides within and is guided by electrically insulating bearing (sleeve) 132 extending through cross head 104 and lining a hole made therethrough. This bearing is illustratively a TEFLON material composite bearing such as a DIXON type CJ bearing manufactured by Dixon Industries Corporation of Bristol, Rhode Island ("TEFLON" is a registered trademark of E. I. DuPont de Nemours and Company in Wilmington, Delaware; "DIXON" is a trademark of Dixon Industries Corporation). As such, shaft 140 is mechanically connected to and moved by cross bar 115 but is electrically insulated from it. The opposite end of shaft 140 abuts against conductive stop plate 143. This stop plate is connected to one end of extension shaft 145. This extension shaft rides within and is guided by bearing 147 which extends through U-shaped cross stop 150. Bearing 147 may also be a DIXON type CJ bearing, though this particular bearing need not be electrically insulating. This shaft is also rigidly connected at its opposite end to anvil 160. This bearing lines a corresponding hole extending axially through the cross stop. The stop plate has a significantly larger diameter than this hole in the cross stop. Piston rod 109, couplers 110 and 110′, shafts 140 and 145, stop plate 143, and anvil 160 are all coaxially aligned and concentric with longitudinal axis 10 (indicated by a dashed line) of the test stand. The portion of specimen 170 situated between anvils 160 and 160′ is the work zone.

With test stand 100 as thusfar described, pneumatic cylinders 111 and 112 are initially set, prior to commencing movement of shaft 109 to compress specimen 170, to appropriately distend piston rods 113 and 114 to move cross bar 115 in the direction shown by arrow 142 such that anvil 160 establishes firm abutting contact with one side of specimen 170. This assures that a low resistance current path will occur between conductor 120 and one side of specimen 170 and specifically through shaft 140, stop plate 143, extension shaft 145 and anvil 160. Cylinders 111 and 112 are operated by appropriately controlling a source of high pressure air (typically on the order of approximately 1 to 6 bar, i.e. 15 to 90 psi) supplied through well-known air regulators (not shown) in order to each provide between 50–400 pounds (approximately 220 to 1800 newtons) of force.

Hydraulic cylinder 105 provides the necessary compressive force to anvil 160 to deform specimen 170 and imparts the necessary speeds to that anvil to obtain desired strain rates in the specimen. Piston rod 109 is connected to coupler 110. Coupler 110′ is securely attached, through a short shaft, to cross bar 115. Both couplers have flat faces and are arranged such that these faces are opposing each other. Specimen compression begins when piston rod 109 has sufficiently moved coupler 110 such that its flat face abuttingly engages the corresponding face of coupler 110′. The resulting motion of both couplers is in the direction shown by arrow 142. Piston rod 109 can be retracted into cylinder 105 in order to permit coupler 110 to freely travel over a finite distance and accelerate prior to striking coupler 110′. High pressure pipes 106 and 107 are connected to inlet and outlet ports of cylinder 105. This cylinder is controlled by a well-known hydraulic servo-control value (not shown) and computer driven control circuits such as those typically found in the GLEEBLE 2000 system manufactured by the present assignee. Inasmuch as servo-control values and associated computer control circuits are all very well known in the art, they will not be discussed any further herein. Pneumatic cylinders 111 and 112 provide a much lower force than does hydraulic cylinder 105. In this regard, the combined force of the pneumatic cylinders may be approximately 800 pounds (approximately 3500 newtons) with the hydraulic cylinder providing as much as approximately 18,000 pounds (approximately 8.3 metric tons) of force. The combined effect of hydraulic and pneumatic cylinders 105, 111 and 112 is to move anvil 160 in the compressive direction at high speed and with high force but in the tension direction (opposite to that shown by arrow 142) at relatively low speed and with a low force.

Specimens to be tested in plane strain by stand 100 are generally rectangular in cross-section and typically vary in thickness from 10 to 40 mm. These specimens will also vary between 14 to 100 mm in width and from 20 to 200 millimeters in height. To assure a substantially uniform temperature gradient (i.e. with very little or no temperature gradients) occurs across the work zone of each plane strain specimen (i.e. the portion of the specimen situated between the anvils) during heating, each of these specimens generally has surface areas for each of two opposing surfaces and a cross-sectional area that are each significantly larger than the contact area between each anvil and each of these surfaces.

The current flow required to heat metallic specimens of these sizes and at heating rates equal to or exceeding rates experienced in modern medium to high speed rolling mills will vary from a few hundred amperes to approximately 22,000 amperes. This electrical current is provided by transformer 130 which provides a source of high current at a low voltage. Though not critical, the transformer should possess a 440 volt, single phase 75 kVA primary with a 5.7 to 10 volt paralleled secondary, preferably controlled by a tap switch, and a 50 or 60 Hz operating frequency. The short circuit output current should be on the order of 50 kA or more. The secondary winding of the transformer is typically formed of one or two turns of a heavy copper casting. By varying the turns ratio of the transformer in finite increments through the tap switch, specimens of different sizes and shapes can be readily heated. Such a transformer is the model G4475NS61S manufactured by Kirkhof Transformer of Grand Rapids, Michigan. Leg 128 of the secondary of transformer 130 is rigidly connected to frame 101 and is secured, via bolt 127, to cross head 104. The other leg, i.e. leg 125, of the transformer is securely connected, via bolts 124, to rolling flexible conductor 122. This conductor, typically, 1.3 cm (approximately 0.5″) in total thickness, is formed of a series of parallel copper laminations, each being approximately 0.13 mm (0.005″) thick and approximately 7.6 cm (3″) wide. Rolling flexible conductors 167 and 167′ are identically formed and have approximately one-half the cross-sectional area of rolling flexible conductor 122. Leads 132 and 132′ are connected to the primary of transformer 130 and carry current thereto from a well-known current supply (not shown). The current supply is a suitable single-phase SCR (silicon controlled rectifier) based thermal control system as is commonly used in the GLEEBLE 2000 system.

Stop bars 154 and 154' are rigidly attached to cross head 104' and, via insulating spacers 152 and 152', to cross stop 150, all of which are contained within a stop assembly. This assures that the cross stop is mechanically connected through the stop bars to cross head 104' but is electrically insulated therefrom. To complete the series electrical current path through specimen 170, rolling flexible conductors 167 and 167' are rigidly attached, via fasteners 169 and 169', to stop bars 154 and 154' and to conductor plate 168. The left side of this plate is secured to anvil support 165 to which anvil 160' is mounted. This anvil abuts against one end of specimen 170. To measure the compressive force or load applied to specimen 170, load cell 174 is situated between the right side of conductor plate 168 and one end of wedge shaft 175. Separate fiber glass washers are situated on both sides of the load cell to insulate it and prevent electrical current from flowing between the load cell and either conductor plate 168 or wedge shaft 175. The load cell is secured along its perimeter by well-known insulated bolts 173 (of which only three are shown for simplicity) extending through both the fiberglass washers and the load cell into conductor plate 168.

Wedge shaft 175 extends from load cell 174 through cross head 104' and runs within and is guided by insulated bearing 177, which may also be a DIXON type CJ bearing. This bearing lines a hole extending completely through this cross head. To further reduce electrical fields near the load cell, wedge shaft 175 is connected through insulated fiberglass washer 179 to wedge yoke 182 situated within wedge assembly 180. This wedge assembly is shown in a cross-section cutaway view for clarity in viewing the action of the wedge and wedge yoke 182. The wedge yoke is securely fastened to wedge shaft 175, as shown in FIGS. 2A-2C, by two insulated bolts (not shown) that extend through rear surface 213 of the wedge yoke. These bolts have insulation situated around their shanks and insulated washers positioned under their heads. These bolts extend through countersunk holes 232 in wedge surface 234, through holes 242 (only one of which is specifically shown) which extend through the body of the wedge yoke, past recess 238 (which accommodates fiberglass washer 179—not specifically shown in this figure) and into an end of wedge shaft 175. As shown, wedge yoke 182 has wedge surface 234 which is inclined on the order of illustratively 17 degrees (to yield approximately a 30% inclination) with respect to the vertical axis of the yoke and is situated between two opposing tongues 211 and 211' that extend in parallel fashion outward of wedge surface 234. Surface 234 abuttingly engages with and slides against complementary shaped surface 224 situated on wedge 184. As shown in FIGS. 1 and 2A-2B, wedge 184 is connected to piston rod 192 which, through hydraulic cylinder 190, moves the wedge vertically up or down. This cylinder is secured to cross head 104' by rigid braces 193. This vertical movement, in the direction shown by arrow 221 in FIGS. 2A and 2B, when translated through the sliding action of the wedge and wedge yoke, causes shaft 175 to move in the direction shown by arrow 223 which, in turn, causes load cell 174, conductor plate 168, anvil 160' and ultimately specimen 170 mounted thereto (all shown in FIG. 1) to move either to the left as shown by arrow 176 or to right in a direction opposite to that shown by this arrow. Anvil 160', anvil support 165, conductor plate 168, load cell 174, shaft 175, washer 179 and wedge yoke 182 are all coaxially aligned with themselves and concentric to longitudinal axis 10 as well as with all the other components, e.g. anvil 160, through which compressive force from cylinder 105 is transmitted to specimen 170.

With reference to FIG. 1, hydraulic cylinder 190 which actuates piston 192 generally provides the same force as that provided during compression testing by cylinder 105, i.e. illustratively on the order of 8.3 metric tons. High pressure pipes 195 and 195' route hydraulic fluid to an inlet port and from an outlet port of cylinder 190. This cylinder is controlled by a well-known hydraulic servo-control value (not shown) and computer driven control circuits such as those typically found in the GLEEBLE 2000 system manufactured by the present assignee. With wedge 184 possessing approximately 17 degrees of slope (again to yield approximately a 30% inclination), wedge shaft 175 only moves approximately 30% as fast and 30% as far as does piston rod 192. As such, wedge 184 multiplies the force of cylinder 190 and in essence provides a very stiff support to anvil 160'. Accordingly, any attempt to push anvil 160' during compression testing in a direction opposite to that shown by arrow 176 is met with mechanical resistance that is much greater than that which is provided by cylinders 105, 111 and 112. Furthermore, the path of mechanical resistance to cross head 104 is short and is through wedge shaft 175, wedge yoke 182, wedge 184 and wedge guide 183 which is bolted securely (though not specifically shown as such) to cross head 104'. Inasmuch as the cross-sectional area of all these components is relatively large, the stress (force/unit area) that occurs therein is kept fairly low. This, in turn, limits the strain in these components to a very small value even at the maximum force provided by hydraulic cylinder 105. Consequently, anvil 160' can be carefully and rapidly positioned by hydraulic cylinder 190 and will thereafter remain in that position even while cylinder 105 is compressing specimen 170 by moving anvil 160 at a high speed and with a high force. Furthermore, the elastic modulus of these components is very high which further reduces the elastic strain that occurs in these components during compression testing of specimen 170.

Wedge assembly 180 also includes two wedge guide plates, wear plate 185 and return springs 187. The wedge guide plates are mirror images of each other and are positioned atop one another. With this in mind and inasmuch as only one guide plate, i.e. plate 183, is shown in FIG. 1 so as to fully expose wedge 184 and wedge yoke 182 within assembly 180, the following discussion will not specifically address the other guide plate. As shown, groove 181, equal in width to approximately one half of the thickness of wedge 184 plus a suitable clearance amount, is cut vertically across wedge guide plate 183. Wedge 184 runs vertically within this groove. Rear surface 226 of the wedge slides against wear plate 185 (which extends out of the plane of the drawing) that is mounted to both guide plates. Groove 178, which is deeper and narrower than groove 181, is cut horizontally within guide plate 183 and perpendicular to groove 181. Groove 178 has a depth equal to approximately one half the width of wedge yoke 182 plus a suitable clearance amount. A tongue of wedge yoke 182, illustratively tongue 211' (see FIGS. 2A-2C), runs within and is guided by groove 178 shown in FIG. 1. As such, both guide plates collectively provide grooves within which the wedge yoke tongues 211 and 211' (see FIGS. 2A-2C) are guided for horizontal movement. Heavy return springs 187 (only one of which is shown in FIG. 1) are connected to the opposing tongues of wedge yoke 182 through threaded holes 225 and 225' shown in FIGS. 2B and 2C. As shown in FIG. 1, these return springs are both compressed against the guide plates and therefore exert a force onto the wedge yoke that pulls the yoke and wedge shaft 175 in a direction opposite to that shown by arrow 176 so as to maintain both the wedge and wedge yoke in intimate contact with each other. These return springs have bolts that extend through the wedge guide plates and wear plate 185 into threaded holes 225 and 225' as shown in FIG. 2C, located in opposing tongues 211 and 211' of wedge yoke 182. As discussed, wedge 184 is not moved while each compressive hit is being made to specimen 170 but rather only during the dwell time between successive hits and specifically while piston rod 109 is being retracted.

Advantageously, wedge assembly 180 can be designed to minimize any force transmitted to cylinder 190 during each compressive deformation of the specimen. In particular, abutting surfaces 234 on the wedge yoke and 224 on the wedge (see FIGS. 1 and 2A-2C), and surface 226 and the corresponding surface on wear plate 185 can each be roughened, such as through sandblasting or other well-known techniques, to provide relatively high amounts of sliding friction therebetween. As such, most of the force transmitted through the wedge during each compressive deformation of the specimen will be expended to overcome the sliding friction existing between these surfaces rather than being applied through piston rod 192 to cylinder 190. Since the wedge is moved while only the pneumatic cylinders alone are exerting a force onto the specimen and particularly during the dwell time existing between successive hits, this sliding friction can be easily overcome by cylinder 190 and hence the wedge can be freely moved to increase the strain that will be imparted to the specimen during the next successive hit. Owing to the substantially greater force produced by hydraulic cylinder 190 through wedge assembly 180 than the combined force produced by both pneumatic cylinders 111 and 112, piston rods 113 and 114 emanating from these pneumatic cylinders are simply pushed back (i.e. forcibly retracted) by movement of the wedge assembly in the direction shown by arrow 176. Consequently, as the wedge assembly incrementally moves specimen 170 to the left by a distance, then the force exerted by the wedge assembly through the specimen simply causes piston rods 113 and 114 to retract into the pneumatic cylinders by the same distance. However, the opposing force that is being simultaneously exerted onto the specimen by the pneumatic cylinders is sufficient to maintain good electrical and thermal contact between both anvils 160 and 160' and specimen 170 and thereby permits heating current to simultaneously flow therethrough. Maintenance of this contact permits the work zone of the specimen to self-resistively heat or conductively cool, as desired, between successive hits.

Stop plate 143, which also forms part of the stop assembly and is mounted to an end of shaft 145, in conjunction with cross stop 150, accurately controls the strain rate imparted to the specimen during each compressive deformation. Specifically, shaft 140, when moved in the compressive direction indicated by arrow 142, abruptly halts its compressive stroke when stop plate 143 impacts against cross stop 150. Inasmuch as the cross stop is rigidly secured through stop bars 154 and 154' to cross head 104', stop plate 143 will immediately stop any forward progress of anvil 160 even if it is compressing specimen 170 at the maximum force supplied by cylinders 105, 111 and 112. Stopping the anvil in this manner assures that the anvil will always stop in an exact physical position at which the true strain rate imparted to the specimen will abruptly drop to zero, regardless of the speed of the anvil in the compressive direction or the force applied to it by cylinders 105, 111 and 112. Inasmuch as the stop plate has a significantly larger diameter than the hole through the cross stop and is relatively thick, the stop plate will not deform when it impacts against cross stop 150. This same stopping procedure is used with each successive hit regardless of the number of times specimen 170 is to be successively compressed.

If specimen 170 is to undergo thermal processing in order to establish a time dependent thermal profile therein, it is necessary to synchronize the desired thermal operation (i.e. the so-called "thermal program") which self-resistively heats and conductively cools the specimen at specified heating and cooling rates to the mechanical operation of the test stand, i.e. the so-called "deformation program". The latter program imparts a pre-defined deformation profile to the specimen.

As discussed above, the specimen is heated by passing a controlled amount of electrical current therethrough. During one half of a cycle of applied AC power, this current (I) flows, as indicated by arrows 401, 403, 405, 407 and 409, from transformer 130, through leg 125 and rolling flexible conductor 122; and through conductor 120, shaft 140, stop plate 143, extension shaft 145 and anvil 160, respectively, to one side of specimen 170. This anvil is maintained in good electrical contact with the specimen while it is being deformed. In order to maintain this contact, as discussed above, pneumatic cylinders 111 and 112 supply a suitable force through cross bar 115 to shaft 140 and hence to anvil 160. This force is applied regardless of the action of hydraulic cylinder 105. This force squeezes the specimen against anvil 160' which is securely held in place by wedge assembly 180. As such, the specimen can not move between the anvils unless the wedge assembly permits such movement. As long as stop plate 142 is not abutting against cross stop 150 but rather is situated apart therefrom, the force applied by the pneumatic cylinders is supported only by specimen 170.

During this half cycle, the return path of the electrical current flowing through specimen 170, as indicated by arrow 411, is initially through anvil 160', anvil support 165 and conductor plate 168. This plate splits the current flow through rolling flexible conductors 167 and 167' (each of which carries approximately one half of the current flow). The current then flows, as indicated by arrows 413 and 415, through stop bars 154 and 154' and recombines in cross head 104'. From there, the current splits once again with approximately one half of the current flowing in each of support columns 102 and 102', as respectively indicated by arrows 419 and 421, and 417 and 425. Inasmuch as these columns are secured to cross head 104, the current will recombine, as illustratively indicated by arrow 425, in this cross head and flow through leg 128 back to transformer 130. Current flow will reverse its direction at successive cycles of applied AC power. Heating current flows through both support columns in the same direction but generates magnetic flux lines ($\phi$) of opposing polarity in the specimen. Both support columns are identically sized, such that an approximately equal amount of heating current flows through each column. Moreover, spatial configuration of the current carrying components in test stand 100 is such that the impedances of the current path through column 102 and that through column 102' are substantially equal. This assures that the total heating current evenly splits between these two columns. In addition, these columns are spatially positioned relative to specimen 170 such that the magnetic fields, as represented by arrows 431 and 433, that encircle these columns and are generated by the heating current flowing therethrough will, in a volumetric region containing the specimen, particularly its work zone, effectively and substantially cancel each other out. Specifically, as is clearly evident, the magnetic fields generated by current flowing in the same direction through columns 102 and 102' oppose each other in the vicinity of the specimen. Since test stand 100 is geometrically configured such that the specimen work zone lies essentially midway between columns 102 and 102', then, with substantially equal amounts of heating current flowing in each of these columns, substantially equal and opposing magnetic fields generated by these columns will substantially cancel each other out in the work zone. This advantageously substantially eliminates induced current flow in the work zone that would otherwise result from these fields. By doing so, substantially all non-uniform current flow throughout the cross-section of the specimen work zone and non-uniform heating that would otherwise result from any such induced current flow are all eliminated thereby assuring that any thermal gradients which appear in the work zone will be very small. Inasmuch as the height of specimen 170 as measured on either side of longitudinal axis 10 of the stand, even after the specimen experiences a shape change during a compressive deformation, remains relatively small when compared with the distance between this axis and either column, substantial cancellation of these magnetic fields will still occur substantially throughout the entire specimen, even after it has been deformed. As such, the specimen will continue to experience essentially uniform heating before, during and after a compressive deformation owing to the flow of heating current therethrough. Furthermore, cancellation of these fields also substantially eliminates any forces from operating on the specimen, before, during and after a compressive deformation, and hence any induced specimen motion that would otherwise result from high currents flowing through these columns. In that regard, if sheet metal specimens that have substantial surface areas are to be used, then producing such a balanced field is essential to eliminate magnetically induced non-uniform heating and magnetically induced motion in the specimen.

To minimize any induced eddy current in and magnetizing of columns 102 and 102' from an external field generated, for example, by current flow through the specimen itself and impinging upon the columns, both of these columns are fabricated from a suitable non-ferrous high strength material, such as various aluminum or stainless steel alloys. Choosing an appropriate non-ferrous material for these columns significantly reduces the magnetic interaction between these columns and the specimen. Furthermore, since the mechanical size and ductility of materials change during heating, columns 102 and 102', conductor 120, shafts 140 and 145, anvil support plate 165 and conductor plate 168 all contain internal cooling passages, preferably for use with water cooling. A sufficient volume of water is pumped through these components at an appropriate rate to assure that the temperature at each interface between the anvil and the specimen does not rise more than approximately 20 degrees C. during heating. This advantageously minimizes any physical expansion of these components and prevents both anvils from softening. Accordingly, a desired final specimen thickness will be accurately reproducible by test stand 100 throughout a series of separate tests.

Transformer leads 125, rolling flexible conductor 122 and conductor 120 are all appropriately positioned, such as that illustratively shown, in order to assure that substantially equal amounts of heating current, as shown by arrow 425, will either recombine to feed leg 128 or be split from the total heating current provided by that leg. Furthermore, all the flexible conductors and leads are typically made as small as possible consistent with the current carrying requirements thereof in order to minimize any magnetically induced motion thereof.

In addition, the cross-section and conductivity of all the current carrying components are chosen such that the entire current path, apart from the specimen, presents a very low electrical resistance and hence a very low voltage drop even at currents on the order of 10 kA or more. By keeping the electrical losses of the current path quite low and inasmuch as the resistance of both the specimen and the interface between the specimen and each anvil are relatively high, most of the electrical power supplied by transformer 130 will be delivered to the specimen. Accordingly, most of the heat caused by this current will be generated in specimen 170.

The temperature of the specimen work zone is measured by thermocouple 171 which is percussion welded to the specimen. Leads 172 which emanate from the thermocouple as that utilized on the GLEEBLE 2000 system. In essence, the temperature of the specimen work zone is compared to a programmed temperature value to generate an error signal within the thermal control system in order to vary the output of transformer 130. The output is varied by an amount sufficient to drive the temperature of the work zone of the specimen to the programmed value as a function of time. Either a well-known pyrometer or other temperature measuring device may readily be substituted for the thermocouple, if desired. The temperature is controlled, as a function of time, and is synchronized to the programmed mechanical deformation of the specimen. By simultaneously controlling both the work zone temperature as well as its physical deformation, my inventive test stand 100 can accurately simulate the action of modern medium to high speed multi-stand rolling mills in the specimen.

Oftentimes, a test stand is required to withstand very large mechanical forces and/or operate with relatively large specimens. In these cases, the stand should be fabricated with more than two, and illustratively four, supporting columns. In accordance with my inventive teachings, the magnetic fields generated by all these columns from the flow of heating current therethrough must substantially cancel in the region of the specimen, particularly its work zone. As such, the columns must all be appropriately sized and positioned to achieve proper current division thereamong and appropriate cancellation of the fields associated therewith. The specific manner through which this is achieved will certainly be readily apparent to anyone skilled in the art based upon my inventive teachings discussed above.

In this regard, FIG. 3 depicts a simplified end view, taken along lines 3—3 and in the direction indicated by the arrows associated therewith shown in FIG. 1, of a second embodiment of my inventive apparatus for inclusion in test stand 100. Here, instead of utilizing two columns 102 and 102' as shown in FIG. 1, the test stand now would contain four such columns. Since all the other details of the stand would be essentially identical to that shown in FIG. 1 and discussed above, this discussion will only address the columns.

As shown in FIG. 3, the test stand would contain cross head 301 (rather than cross head 104 as depicted in FIG. 1) to which four identically sized conductive columns 311, 313, 315 and 317 would be mounted symmetric to conductive shaft 140, with each column situated in the vicinity of a different corner of cross head 301. As discussed above, shaft 140 would be aligned concentric with a longitudinal axis of the stand. Moreover, each of these columns and shaft 140 would contain an internal cooling passage, such as passage 335 in shaft 140. These four columns would be symmetrically located with respect to the specimen (not specifically shown in this figure). The columns would each be appropriately sized and located such that the impedance of the current path through each of these columns would be substantially equal thereby permitting the total heating current to be equally divided into four portions among these columns. As such, the magnetic fields generated by these columns would be substantially equal and directed as indicated by arrows 321, 323, 325 and 327, for that half cycle of the current flowing into the plane of the figure. This current is indicated by an "X" symbol, illustratively symbol 343, within each of these columns. By symmetrically positioning the columns and assuring equal current division thereamong, these fields will substantially cancel in the volumetric region containing the specimen, particularly its work zone. Thus, by proper selection of the geometry of each column and its placement, particularly in conjunction with other high current carrying components in the test stand, non-uniform magnetic fields resulting from the passage of heating cut through the test stand can still be substantially eliminated regardless of the number of such columns being used.

Heating current will flow in the reverse direction within shaft 140, i.e. out of the plane of the figure, as indicated by dot 341, for the current half cycle of the current. During this half cycle, heating current flowing through the specimen itself will generate a magnetic field having flux lines oriented in the direction shown by arrow 329 and opposite to the field generated by each of the columns. The directions of all the fields will simply reverse during the next cycle of heating current.

Furthermore, since the columns themselves serve as conductors for the heating current, the design and construction of a test stand in accordance with my inventive teachings is simplified over designs known in the art which rely on using external cables or other conductors to carry the heating current.

Moreover, if, for some reason, all the columns can not be chosen to have a substantially identical size, particularly a cross-sectional area, then the location of the columns can be appropriately modified, such as by positioning the location of the differently sized column accordingly and non-symmetrically with respect to the other columns and the longitudinal axis of the stand. Furthermore, the cross-heads need not carry heating current. Instead, suitable wired connections could be used to route heating current among these columns, the stop bars and transformer. Unfortunately, doing so would necessitate additional manufacturing cost and complexity as well as require these wires to be carefully positioned in order for them to avoid experiencing magnetically induced motion resulting from heating currents passing through the test stand and specimen.

Clearly, while test stand 100 deforms a test specimen using compressive deformation, it should now be apparent to those skilled in the art that my invention can be easily incorporated into a test stand designed to impart either compressive and/or tensile forces to a specimen under test. In addition, though test stand 100 utilizes single-phase power line (60 Hz) heating currents, heating currents at other appropriate frequencies and phases (such as three phase) can be readily used. Advantageously, substantial cancellation of any resulting magnetic fields will still occur throughout a volumetric region containing the specimen thereby significantly reducing any magnetically induced heating currents in the specimen and magnetically induced specimen motion.

Although two preferred embodiments which incorporate the teachings of my present invention have been shown and described in detail herein, those skilled in the art can readily devise many other varied embodiments that still incorporate these teachings.

I claim:

1. Apparatus for a thermal-mechanical material testing system, wherein said system controllably imparts a desired deformation to a conductive test specimen and controllably heats said test specimen to a desired temperature through self-resistive heating, said apparatus comprising:

a test stand, having a longitudinal axis associated therewith, comprising:

deforming means, concentrically aligned with the longitudinal axis, for securely holding a conductive test specimen of a predefined size, for imparting a pre-defined controlled force along said axis to the test specimen in order to cause the test specimen to undergo a desired deformation and for establishing an electrical current path through the specimen;

a fixed frame situated about said deforming means and having first and second spaced apart supporting members and a plurality of electrically conductive columnar members arranged parallel to said longitudinal axis and situated between and securely connected to said first and second supporting members, said deforming means situated being securely mounted to said second supporting member, and said deforming means being in conductive electrical communication with all of said columnar members;

wherein, to self-resistively heat the test specimen, electrical heating current is to be applied from an external source serially through said deforming means, said test specimen and said plurality of columnar members, and wherein the plurality of conductive columnar members are arranged between said first and second supporting members and in a pre-determined manner about said longitudinal axis such that magnetic fields generated by all of said conductive columnar members and resulting from the electrical heating current flowing therethrough will substantially cancel each other in a volume containing the test specimen, whereby the test specimen will experience neither any appreciable magnetically induced non-uniform heating nor any appreciable magnetically induced motion while the heating current flows through the stand.

2. The apparatus in claim 1 wherein the plurality of conductive columnar members are all substantially identical in size and are arranged symmetric with respect to the longitudinal axis of said stand.

3. The apparatus in claim 2 wherein each of the conductive columnar members is fabricated from a conductive non-ferrous material.

4. The apparatus in claim 3 wherein said first and second supporting members are electrically conductive and arranged perpendicular to the longitudinal axis; and the external source comprises a power supply, connected between said deforming means and said first conductive supporting member, for providing line frequency current as the heating current.

5. The apparatus in claim 4 wherein each one of the conductive columnar members has an internal cooling passage.

6. The apparatus in claim 5 wherein said deforming means comprises:
   force producing means, having a first actuator and mounted to the fixed frame, for controllably generating a mechanical force along a first pre-defined direction;
   first and second deformation producing means for compressively deforming the test specimen so as to generate a compressive deformation therein, wherein said first and second deformation producing means abuttingly engage with corresponding opposing sides of the test specimen while the test specimen is being deformed;
   force transferring and stopping means, situated in abutting engagement with said first deformation producing means, for moving said first deformation producing means, in response to said force, along said first pre-defined direction so as to compressively deform said test specimen and for terminating further movement of said fight deformation producing means as soon as said first deformation producing means has compressed the test specimen by a pre-determined amount; and
   moving means, having a second actuator and mounted to said second supporting member and coupled through said second supporting member to said second deformation producing means and operative in response to the second actuator, for moving said specimen and said first and second deformation producing means by the pre-determined amount and in a second direction opposite to the first pre-defined direction prior to commencement of said compressive deformation, wherein said moving means experiences substantially no movement in said first pre-defined direction while said specimen is being compressively deformed;
whereby strain rate and final strain induced in the specimen during said compressive deformation are respectively and substantially independently determined by velocity of said force transferring and stopping means along said first direction during said deformation and a distance that said moving means is moved in said second pre-defined direction prior to said deformation.

7. The apparatus in claim 6 wherein the moving means comprises:
   a wedge shaft connected at one end to said second deformation producing means and extending in said first direction therefrom;
   a wedge having a first inclined surface;
   a wedge guide fixedly connected to said frame for guiding movement of said wedge along third and fourth directions, said third and fourth directions being opposite to each other and substantially perpendicular to said first and second directions;
   a wedge yoke connected to said wedge shaft at a second end thereof and having a second inclined surface complementary to said first inclined surface for slidably engaging with said first inclined surface so as to move said wedge yoke in either said first or second directions as said wedge yoke is moved in said third or fourth directions, wherein said wedge yoke moves at a pre-defined proportion of distance and rate at which said wedge moves while in sliding engagement therewith; and
wherein the second actuator is connected to said wedge at one end thereof for controllably moving said wedge through a desired distance in either said third or fourth directions.

8. The apparatus in claim 7 wherein said wedge guide comprises:
   a first groove situated along said third and fourth directions for guiding said wedge for movement therealong; and
   a second groove intersecting with and substantially perpendicular to said first groove for guiding said wedge yoke along said first and second directions in response to movement of said wedge.

9. The apparatus in claim 8 wherein said wedge yoke comprises: first and second tongues, each of which is situated on one side of said inclined surface and both of which extend in a parallel direction outward therefrom; and said wedge guide comprises first and second return springs fixedly mounted to said wedge guide and to corresponding ones of said tongues for exerting a force onto said wedge yoke.

10. The apparatus in claim 7 wherein said first and second actuators respectively comprise first and second servo-controlled hydraulic cylinders.

11. The apparatus in claim 10 wherein said frame comprises first and second cross heads, as respectively said first and second supporting members, spaced apart and electrically and mechanically connected together, in a fixed arrangement, by said plurality of conductive columnar members, said first and second cross-heads having first and second holes extending therethrough in said first pre-defined direction and a first insulating bearing lining said first hole; and said apparatus further comprises:
   a pair of third and fourth cylinders securely connected to said first cross-head and having first and second piston rods; and
   said force transferring and stopping means further comprises:
   a cross bar having two opposing ends and fixedly connected to said first and second pistons in the vicinity of the two opposing ends thereof, said cross bar further having a coupler for abuttingly engaging with a corresponding coupler attached to an end of a piston of said first cylinder and transferring the mechanical force produced therefrom to said specimen so as to produce the compressive deformation thereof;
   an insulating plate fixedly connected at one surface of said plate at substantially a center axial location thereof to said cross bar;
   first and second conductive extension shafts, said first extension shaft extending through the first insulating bearing located in said first cross-head so as to be electrically insulated from said first cross head;

a rigid conductor fixedly and electrically connected between a second surface of said insulating plate, opposite to said first surface thereof, and a first end of said first extension shaft;

a substantially U-shaped cross stop having a third hole located axially therethrough and a second bearing lining said third hole for guiding said second shaft along said first and second directions but electrically insulating said second shaft from said cross head;

a stop plate fixedly secured to a first end of said second shaft and situated between a second end of said first shaft and the first end of said second shaft, wherein the stop plate has a diameter greater than that of the third hole and functions to impact against said cross stop during movement of said second shaft in the first direction so as to abruptly halt further movement of said second shaft in said first direction during compressive deformation of said specimen; and first and second stop bars fixedly securing, through corresponding first and second insulating spacers, said cross top to the second cross head; and wherein the cross bar, in response to a force exerted thereon by said pair of third and fourth cylinders, establishes and maintains an abutting series electrical current path through said rigid conductor, said first and second conductive shafts and said specimen, said cross bar being electrically insulated from said path; and wherein said first and second deformation producing means respectively comprises first and second electrically conductive anvils, the first anvil being securely mounted to a second surface of said second extension shaft, and the second anvil being mounted to a conductive anvil supported located within said deformation producing means; and wherein said first and second extension shafts, said stop plate and said first and second anvils are in substantial coaxial alignment.

12. The apparatus in claim 11 wherein said power supply comprises a low voltage high current transformer having a secondary winding which is connected between said rigid conductor and said first cross-head so as to provide a controlled source of the electrical heating current to said test specimen.

13. The apparatus in claim 11 wherein said second deformation producing means further comprises:

a conductive plate having first and second opposing sides and in electrical communication with said second cross head;

the conductive anvil support having first and second opposing surfaces and mounted at the first surface thereof to the first side of said conductive plate; said second anvil being mounted to the second surface of said conductive anvil support;

a load cell having first and second opposing surfaces wherein the first surface of the load cell is mounted to the second side of said conductor plate; and said wedge shaft being securely mounted to the second surface of the load cell; and wherein said second anvil, the conductive anvil support, the load cell and the wedge shaft are all in substantial coaxial alignment.

14. The apparatus in claim 6 wherein the moving means comprises:

a shaft connected at one end to said second deformation producing means and extending in said first direction therefrom; and wherein the second actuator is fixedly mounted to said frame and connected to a second end of said shaft.

15. The apparatus in claim 14 wherein said first and second actuators respectively comprise first and second servo-controlled hydraulic cylinders.

16. The apparatus in claim 15 wherein said frame comprises first and second cross heads, as respectively said first and second supporting members, space apart and electrically and mechanically connected together, in a fixed arrangement, by said plurality of conductive columnar members, said first and second cross-heads having first and second holes extending therethrough in said first pre-defined direction and a first insulating bearing lining said first hole; and said apparatus further comprises: a pair of third and fourth cylinders securely connected to said first cross-head and having first and second piston rods; and said force transferring and stopping means further comprises:

a cross bar having two opposing ends and fixedly connected to said first and second pistons in the vicinity of the two opposing ends thereof, said cross bar further having a coupler for abuttingly engaging with a corresponding coupler attached to an end of a piston of said first cylinder and transferring the mechanical force produced therefrom to said specimen so as to produce the compressive deformation thereof;

an insulating plate fixedly connected at one surface of said plate at substantially a center axial location thereof to said cross bar;

first and second conductive extension shafts, said first extension shaft extending through the first insulating bearing located in said first cross-head so as to be electrically insulated from said first cross head;

a rigid conductor fixedly and electrically connected between a second surface of said insulating plate, opposite to said first surface thereof, and a first end of said first extension shaft;

a substantially U-shaped cross stop having a third hole located axially therethrough and a second bearing lining said third hole for guiding said second shaft along said first and second direction but electrically insulating said second shaft from said cross head;

a stop plate fixedly secured to a first end of said second shaft and situated between a second end of said first shaft and the first end of said second shaft, wherein the stop plate has a diameter greater than that of the third hole and functions to impact against said cross stop during movement of said second shaft in the first direction so as to abruptly halt further movement of said second shaft in said first direction using compressive deformation of said specimen; and first and second stop bars fixedly securing, through corresponding first and second insulating spacers, said cross top to the second cross head; and wherein he cross bar, in response to a force exerted thereon by said pair of third and fourth cylinders, establishes and maintains an abutting series electrical current path through said rigid conductor, said first and second conductive shafts and said specimen, said cross bar being electrically insulated from said path; and wherein said first and second deformation producing means respectively comprise first and second electrically conductive anvils, the first anvil being securely mounted to a second surface of said second extension shaft, and the second anvil being mounted to a conductive anvil support located within said deformation producing means; and wherein said first and second extension shafts, said stop plate and said first and second anvils are in substantial coaxial alignment.

17. The apparatus in claim 16 wherein said power supply comprises a low voltage high current transformer having a secondary winding which is connected between said rigid conductor and said first cross-head so as to provide a controlled source of electrical heating current to said specimen.

18. The apparatus in claim 16 wherein said second deformation producing means further comprises:
- a conductive plate having first and second opposing sides and in electrical communication with said second cross head;
- the conductive anvil support having first and second opposing surfaces and mounted at the first surface thereof to the first side of said conductive plate; said second anvil being mounted to the second surface of said conductive anvil support;
- a load cell having first and second opposing surfaces, wherein the first surface of the load cell is mounted to the second side of said conductor plate; and
- said wedge shaft being securely mounted to the second surface of the load cell; and wherein said second anvil, the conductive anvil support, the load cell and the wedge shaft are all in substantial coaxial alignment.

* * * * *